United States Patent
Park

(10) Patent No.: US 9,770,224 B2
(45) Date of Patent: Sep. 26, 2017

(54) STETHOSCOPE ADAPTER SYSTEM FOR A HEADSET MICROPHONE

(71) Applicant: Humingdoc, LLC, Reno, NV (US)

(72) Inventor: Paul Park, Reno, NV (US)

(73) Assignee: HUMMINGDOC, LLC, Reno, NV (US)

( * ) Notice: Subject to any disclaimer, the term of this patent is extended or adjusted under 35 U.S.C. 154(b) by 0 days.

(21) Appl. No.: 15/271,143

(22) Filed: Sep. 20, 2016

(65) Prior Publication Data

US 2017/0079612 A1   Mar. 23, 2017

Related U.S. Application Data

(60) Provisional application No. 62/221,054, filed on Sep. 20, 2015.

(51) Int. Cl.
*A61B 7/04* (2006.01)
*H04R 1/46* (2006.01)
*H04R 1/34* (2006.01)

(52) U.S. Cl.
CPC ............... *A61B 7/04* (2013.01); *H04R 1/342* (2013.01); *H04R 1/46* (2013.01)

(58) Field of Classification Search
CPC ...................................................... A61B 7/04
See application file for complete search history.

(56) References Cited

U.S. PATENT DOCUMENTS

| | | | | |
|---|---|---|---|---|
| 6,498,854 B1* | 12/2002 | Smith | ...................... | A61B 7/04 381/67 |
| 2009/0232323 A1* | 9/2009 | Berk | ........................ | A61B 7/04 381/67 |
| 2009/0242364 A1* | 10/2009 | Prest | .................... | H01H 9/0228 200/16 D |
| 2009/0279708 A1* | 11/2009 | Habboushe | .......... | A61B 5/0002 381/67 |
| 2011/0087135 A1* | 4/2011 | Ferzli | ....................... | A61B 7/04 600/586 |
| 2011/0096936 A1* | 4/2011 | Gass | ........................ | A61B 7/04 381/67 |
| 2011/0103606 A1* | 5/2011 | Silber | .................. | H04R 1/1033 381/74 |
| 2014/0105441 A1* | 4/2014 | Kroupa | .............. | B65H 75/4434 381/370 |

(Continued)

*Primary Examiner* — Olisa Anwah
(74) *Attorney, Agent, or Firm* — Mark A. Goodman, Esq.

(57) ABSTRACT

An adapter system that converts an in-line microphone to a stethoscope is described. The adapter includes a grooved channel, a rear cap, a front diaphragm, a recessed surface and a sound tunnel. The grooved channel may be disposed in a base. The grooved channel receives the in-line microphone. The lid covers the grooved channel and the lid is removably coupled to the base. The front diaphragm contacts a listening surface. Also, the front diaphragm is coupled to the base. The recessed surface is disposed adjacent to the front diaphragm. The sound tunnel includes a sound tunnel entrance proximate to the recessed surface. The sound tunnel extends to the grooved channel. The recessed surface and the sound tunnel capture sound vibrations received at the front diaphragm and transmit the sound vibrations through the sound tunnel to the in-line microphone disposed in the grooved channel.

27 Claims, 14 Drawing Sheets

(56) References Cited

U.S. PATENT DOCUMENTS

| | | | |
|---|---|---|---|
| 2014/0155762 A1* | 6/2014 | Maskara | A61B 7/003 600/484 |
| 2014/0254814 A1* | 9/2014 | Van Alstine | A61B 7/02 381/67 |
| 2014/0270218 A1* | 9/2014 | Wang | A61B 7/04 381/67 |
| 2015/0190110 A1* | 7/2015 | Chong | H04R 1/46 600/528 |
| 2015/0201272 A1* | 7/2015 | Wong | H04R 1/46 381/67 |

\* cited by examiner

STETHOSCOPE ADAPTER SYSTEM FOR A HEADSET MICROPHONE

CLAIM OF BENEFIT TO EARLIER FILED PROVISIONAL APPLICATION

This application claims the benefit of provisional application No. 62/221,054, filed on Sep. 20, 2015.

FIELD

This description relates to a stethoscope adapter system for a headset microphone. More particularly, the description relates to a temporary or permanent stethoscope adapter for a pre-existing microphone associated with a headset, in which the stethoscope adapter and pre-existing microphone are communicatively coupled with a CPU containing device.

BACKGROUND

Stethoscopes are medical devices that capture, focus, and transmit sound waves produced by dynamic organs and vessels of humans or animals so that a clinician can hear and interpret the audible sounds produced by the organs or vessels. This process is termed auscultation and is a common means for diagnosis of pathologic conditions through detection of abnormal sounds that are characteristic for the disease states. In conventional stethoscopes, the microscopic movements of the diaphragm translate into increases in air pressure resulting in sound waves that travel through the tubing to the listener's ears. In contrast, electronic stethoscopes typically incorporate a microphone, capacitive sensor, or piezo-electric sensor juxtaposed to the stethoscope diaphragm that detect the acoustic waves for conversion into electrical signals for digitalization, filtration processing, and amplification. There are several advantages of the electronic stethoscopes, including digitalization of analog sound so that the sound data can be saved or transmitted via the internet to facilitate remote diagnostic capabilities in telemedicine. The electronic stethoscopes that utilize a microphone have traditionally suffered from excessive ambient noise detection and inefficient sound energy transfer. For instance, the "Digital Stethoscope" from http://www.thingiverse.com/thing:266767 shows a permanent enclosure of an earphone capable of recording pulmonary but not cardiac sounds. Likewise, the "MakerSenga" from http://www.thingiverse.com/thing:34110 is a fetal stethoscope that is conical in shape with a microphone placed at one end, which connects to the smartphone via a 3.5 mm port. The latter embodiment lacks a diaphragm and is significantly elongated and larger in size compared to a traditional chestpiece making it less portable than traditional stethoscopes.

The "iPhone Stethoscope Attachment" from http://www.thingiverse.com/thing:149028 shows an adapter that enables the attachment of the tubing of a conventional (non-electronic) stethoscope to the integrated microphone of iPhone 4 or 5. However, since the latter embodiment connects to lengthy tubing attached to the chestpiece of a stethoscope, a significant amount of the sound signal deteriorates prior to reaching the microphone of the iPhone. Furthermore, an intact stethoscope must be cut and essentially destroyed in order to create the digitized stethoscope. The limited quality of sound capture is apparent in the test recording on http://soundcloud.com/jeffthompson/3d-printed-iphone-stehoscope, which fails to demonstrate audible heart sounds.

The "Eko Core" from Eko Devices (https://ekodevices.com/) is also an attachment to the tubing of a conventional stethoscope. However, the latter embodiment differs from the "iPhone Stethoscope Attachment" in that it captures and digitizes sound for transmission via Bluetooth to a CPU utilizing device and offers the user to listen in analog or digital mode through the conventional stethoscope. As with the "iPhone Stethoscope Attachment," the "Eko Core" requires the ownership and cutting (and therefore partial destruction) of the tube of a traditional stethoscope, which further adds to the cost of electronic device itself.

The "Steth IO" (release pending) from StratoScientific, Inc. (http://www.stethio.com/) is a smartphone case with an integrated stethoscope chestpiece and diaphragm, which also captures body sounds that are funneled to the microphone of the smartphone for "visualization, ambient noise reduction, and amplification." The 3.5 mm port is accessible in the "Steth IO" so that body sounds can be heard through earphones, headsets, or speakers. However, since the diaphragm and chestpiece is fixed to the opposite side of the smartphone screen in its design, direct visualization of the real-time phonocardiogram displayed on the smartphone is limited by the user if the said user is an individual who was using the embodiment on oneself, e.g., for telemedicine purposes. Furthermore, since the StethIO utilizes the microphone integrated into the smartphone, it cannot not be connected directly to another CPU containing device such as a desktop or laptop computer.

The "Thinklabs One Digital Stethoscope" (http://www.thinklabs.com; U.S. Pat. No. 6,498,854 B1, PCT/US 2000/041633, US 2005/0058298 A1, US 2006/0018487 A1) is an electronic stethscope that consists of a chestpiece, which contains a capacitive plate that senses the vibrations of a capacitive Electromagnetic Diaphragm, thereby translating mechanical vibrations into audio signals through voltage changes. The latter embodiment can be used as a stand-alone stethoscope with a headset, or it can connect to a smartphone for capture and/or processing of the digitalized sound data. The body sounds can be heard and captured on the smartphone in real-time with a connection splitting adapter for the Thinklabs One Digital Stethoscope. Although the latter embodiment may produce superior sound quality with less ambient noise capture for digitalization, the production cost is likely to be significantly higher than attachments that funnel sound to an existing microphone. This may also be the case for the "CliniCloud Stethoscope" (https://clinicloud.com), which at the time of this writing has not yet been released.

There has been little or no development of a cost-efficient stethoscope adapter for the microphone of already existing earphones or headset listening device that will temporarily convert the microphone containing earphones or headset listening device attached to a CPU containing device into a electronic stethoscope capable of capturing the full range of bodily sounds, including lungs, heart, and bowel sounds with ambient noise reduction as well as simultaneous recording and listening capabilities of the digitalized sounds through earphones or headset listening device and real-time visualization on the CPU containing device such as a smartphone.

SUMMARY

An adapter that converts an inline microphone to a stethoscope is described. The adapter includes a grooved channel, a lid (which may sometimes be referred to as a "rear cap"), a front diaphragm, a recessed surface and a sound tunnel. The grooved channel is disposed in a base. The grooved channel receives the inline microphone. The lid covers the grooved channel and the lid is removably coupled to the base. The front diaphragm contacts a listening surface. Also, the front diaphragm is coupled to the base. The recessed surface is disposed adjacent to the front diaphragm. The sound tunnel includes a sound tunnel entrance proximate to the recessed surface. The sound tunnel extends to the grooved channel. The recessed surface and the sound tunnel capture sound vibrations received at the front diaphragm and transmit the sound vibrations through the sound tunnel to the inline microphone disposed in the grooved channel.

DRAWINGS

The present invention will be more fully understood by reference to the following drawings which are for illustrative, not limiting, purposes.

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and apparatus described hereinafter may vary as to configuration and as to details. Additionally, the methods may vary as to details, order of the actions, or other variations without departing from the illustrative methods disclosed herein.

The apparatus presented herein relates to stethoscopes, specifically to an adapter that will temporarily convert the microphone of earphones or a headset listening device connected by wire or wirelessly to a CPU containing device capable of capturing and processing bodily sound data and transmitting the data via the internet to a remote location.

Figure 1:
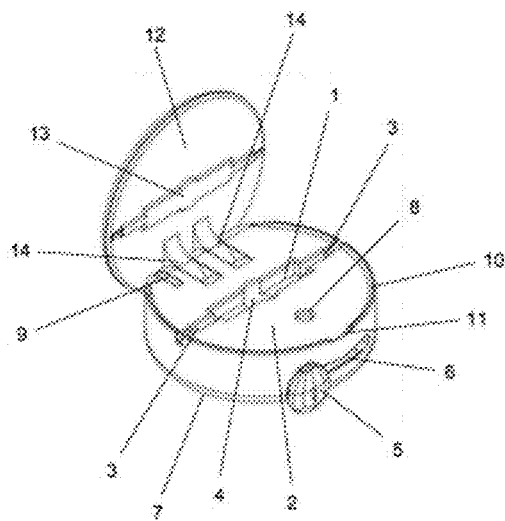
FIG. 1 shows a perspective view of an illustrative fully assembled stethoscope microphone adapter with the lid open revealing the temporary sound chamber.

Referring to FIG. 1 there is shown a perspective view of an illustrative fully assembled stethoscope microphone adapter with the lid 12 open revealing the temporary sound chamber. The adapter includes a grooved channel 1, a lid 12, a front diaphragm, a recessed surface and a sound tunnel. The grooved channel 1 may be disposed in a base 2 or in the lid. The grooved channel 1 receives an inline microphone. Herein, an inline microphone is defined as a microphone that's wired as part of a headphone cable. The microphone may be position at any point of the headphone cable. The lid 12 covers the grooved channel 1 and the lid 12 is removably coupled to the base 2. The front diaphragm 18 contacts a listening surface, e.g., the chest of a human being or an animal. Also, the front diaphragm 18 is coupled to the base 2. The recessed surface 22 is disposed adjacent to the front diaphragm 18. The sound tunnel 4 includes a sound tunnel entrance proximate to the recessed surface 22. The sound tunnel 4 extends to the grooved channel 1. The recessed surface 22 and the sound tunnel 4 capture sound vibrations received at the front diaphragm and transmit the sound vibrations through the sound tunnel 4 to the inline microphone (not shown) disposed in the grooved channel 1.

Figure 3:
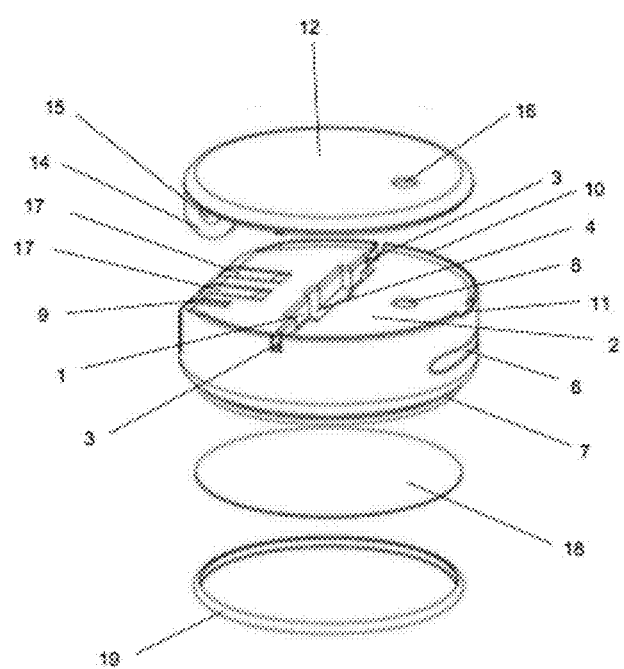
FIG. 3 shows a perspective view of the overall assembly layout of the preferred embodiment of the stethoscope microphone adapter of FIG. 1 and FIG. 2.
Figure 4:
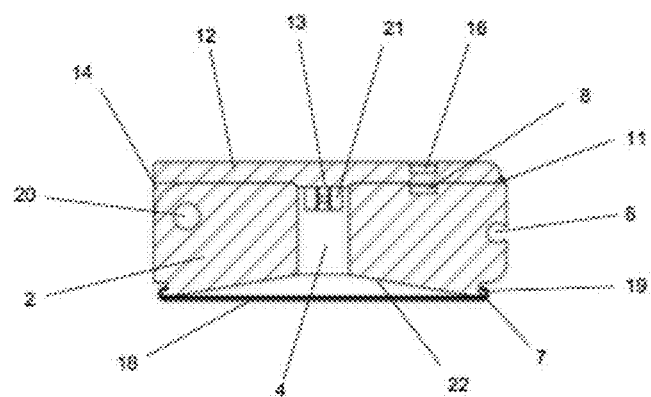
FIG. 4 shows a cross-sectional view of the stethoscope microphone adapter of FIG. 1 with the lid closed.

More specifically, the base 2 of the stethoscope adapter has a groove 1 for the housing of the microphone of a pre-existing headset. The groove 1 for the microphone is flanked by grooves 3 for the wires that extend from the microphone to the 3.5 mm connector and earbud, respectively. The groove 1 for the microphone connects to the sound tunnel 4, which assists with the filtration, amplification, and transmission of collected sounds. The side of the base 2 contains a groove 6 into which an extraneous earbud 5 can be placed. The top of the base 2 has an elevated rim 10, which follows the contour of the lid. The discontinuity 11 of the elevated rim 10 enables easy access to the closed lid for reopening. The bottom of the base 2 also has a notched edge 7, which facilitates securing of the diaphragm 17 by a concave semi-flexible ring 18 or tape (FIGS. 3 and 4). The base 2 also contains slots 17 (FIG. 3) for the hinge 14 protruding from the lid 12 and a slotted opening 9 to facilitate placement of a retaining ring onto a grooved clevis pin 19 (FIG. 4), which secures the lid 12 to the base 2 by traveling through the holes 15 of the lid hinge 14 and the base 2. The base 2 contains a small magnet 8 that is recessed into the base so that it is flush with the top surface of the base 2. The lid 12 of the stethoscope microphone adapter contains a protrusion 13, which corresponds to the shape and contour of the grooves 1 for the microphone, grooves 3 for the extending wires, and sound tunnel 4.

Figure 2:
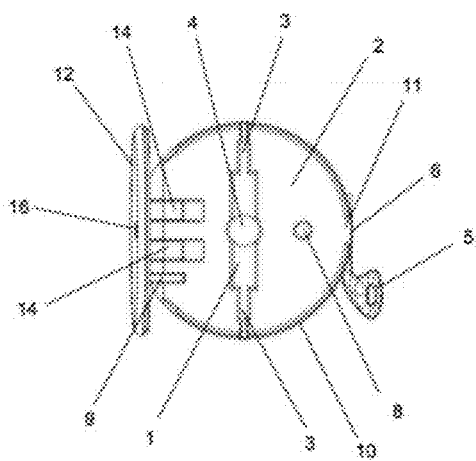
FIG. 2 shows a top view of the fully assembled stethoscope microphone adapter of FIG. 1.

FIG. 2 is a perspective top view of the stethoscope microphone adapter showing the features described for FIG. 1. Note the enlarged diameter (9-11 mm) of the circular sound tunnel 4 that is located in the center of the groove for the microphone of a pre-existing headset. The view in FIG. 2 also shows a small magnet 16 that is recessed into the top surface of the lid, which facilitates closure of the lid by attractive forces with the magnet 8 recessed into the base 2.

FIG. 3 is a perspective bird's eye top view of the individual components of the unassembled stethoscope microphone adapter. The curved extensions 14 from the lid 12 slide into the corresponding slots 17 in the base 2. Note the diaphragm 18, which can be composed of plastic, nylon, or metal. The diaphragm 18 is secured to the bottom notched edge 7 of the base 2 by a concave semi-flexible ring 19 made of rubber, silicone, or plastic. Alternatively, the diaphragm can be secured by adhesive tape 19.

FIG. 4 is a sagittal cross-sectional view through the center of the stethoscope microphone adaptor with the lid closed. The protruding element from the lid 13 facilitates in forming a sealed sound chamber 21, which houses the microphone. Note the wide conical shape of the bottom 22 of the base 2 connecting to the wide bore sound tunnel 4, which facilitate optimal capture of desirable sound waves transmitted through the diaphragm 18. The body of the base 2, which facilitates ambient noise reduction, can be made of plaster, ceramic, plastic, metal, or wood. Based can also be in a shelled out or hollow form for molded plastic for weight and cost reduction. Note also the clevis pin 20 that goes through the holes 15 in the lid extensions 14 and base 2 to create the secure rotating hinge. The proximity of the magnet 16 in the lid 12 and magnet 8 in the base 2 keeps the lid closed and allows easy opening.

Figure 5:
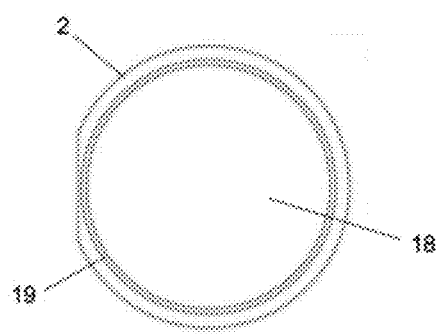
FIG. 5 shows a bottom view of the stethoscope microphone adapter of FIGS. 1 through FIG. 4 with the diaphragm in place.

FIG. 5 is a perspective bottom view of the stethoscope microphone adapter of FIGS. 1-4 with the diaphragm 18 secured in place by the semi-flexible concave circular ring or tape 19. Note the widened diameter (60 mm) of the diaphragm 18, which facilitates more robust capture of sound signals, especially the lower frequencies that correspond to heart sounds. The diaphragm 18 can be made of plastic, nylon, or metallic materials. The preferred embodiment contains a polyethylene terephthalate (PETE) plastic diaphragm 18 that is less than 0.45 mm in thickness. The thinner diaphragm also facilitates more robust capture of lower frequency heart sounds.

Figure 6:
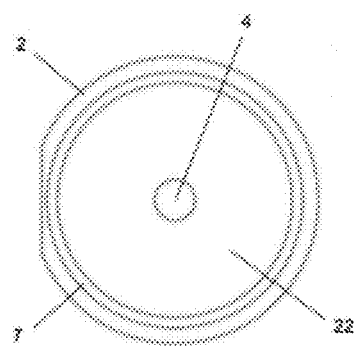
FIG. 6 shows a bottom view of the stethoscope microphone adapter of FIGS. 1 through FIG. 5 without the diaphragm.

FIG. 6 is a perspective bottom view of the stethoscope microphone adapter of FIGS. 1-4 without the diaphragm and securing concave circular ring or tape 19. Note the enlarged sound tunnel 4 (9-11 mm in diameter; 12-14 mm in length), which is continuous with the wide conical bottom 22 (60 mm in diameter) of the stethoscope adapter base 2.

Figure 7:
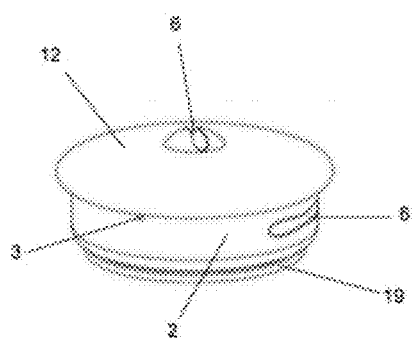
FIG. 7 shows is a perspective top view of a second illustrative embodiment of the fully assembled stethoscope microphone adapter having a cap that twists onto the adapter base.

FIG. 7 is a perspective bird's eye top view of a fully assembled alternative embodiment of the stethoscope microphone adapter with a twist-on lid 12. The center of the lid 12 and the side of the base 2 contains a groove 6 for an extraneous earbud. The wires connected to the microphone exist from the predefined grooves 3 for the wires.

Figure 8:
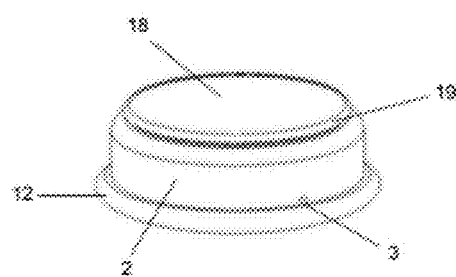
FIG. 8 shows a perspective bottom view of the second illustrative embodiment of FIG. 7 having a widened diaphragm (60 mm in diameter).

FIG. 8 is a perspective bird's eye bottom view of the fully assembled alternative embodiment of the stethoscope microphone adapter of FIG. 7. Note the widened diaphragm 18 (60 mm in diameter) secured to the base 2 of the adapter by a semi-flexible concave circular ring or tape 19.

Figure 9:
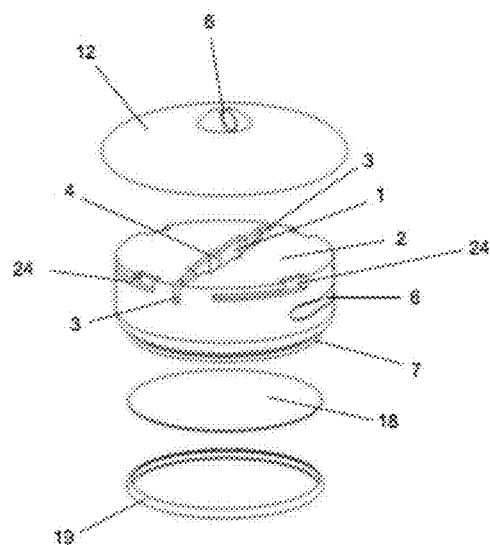
FIG. 9 shows a perspective top view of the overall assembly layout of the embodiment presented in FIG. 7 and FIG. 8.

FIG. 9 is a perspective bird's eye top view of the individual components of the unassembled stethoscope microphone adapter. The protrusions 23 (FIG. 10) from the lid 12 enter into the lock-in grooves 24 of the base 2 and then slides into place with a twisting motion to secure the lid 12 to the base 2. The lid 12 can be reopened by twisting in the opposite direction.

Figure 10:
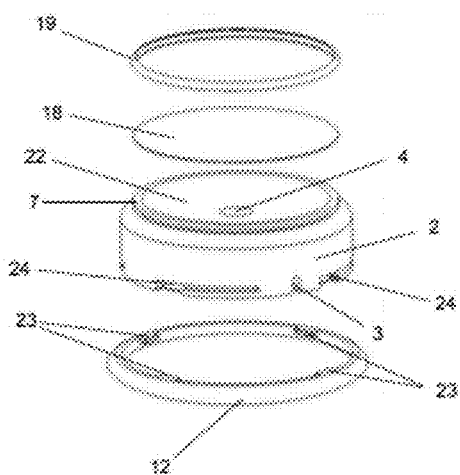
FIG. 10 shows a perspective bottom view showing of the overall assembly layout of the embodiment shown in FIGS. 7 through FIG. 9.

FIG. 10 is a perspective bird's eye bottom view of the individual components of the unassembled stethoscope microphone adapter. Note the grooves on the base of the adapter that allows the cap to twist and lock into place. Note that this embodiment does not contain a contoured protrusion from the lid 13 (FIG. 1) that corresponds to the shape and contour of the grooves 1 (FIG. 1) for the microphone, grooves 3 (FIG. 1) for the extending wires, and sound tunnel 4 (FIG. 1).

Figure 11:
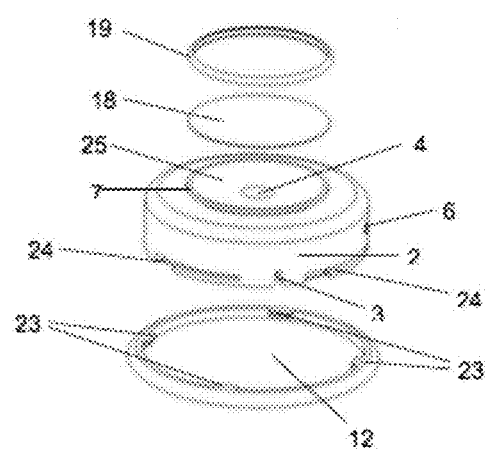
FIG. 11 shows a perspective bottom view showing the overall assembly layout of the embodiment of the stethoscope microphone adapter of FIGS. 7 through FIG. 10 with a smaller conical bottom and diaphragm (44 mm in diameter).

FIG. 11 is a perspective bird's eye bottom view of the individual components of the unassembled stethoscope microphone adapter embodiment similar to that of FIGS. 7-10 except with a smaller conical base bottom 25 and diaphragm 18 (44 mm in diameter).

Figure 12:
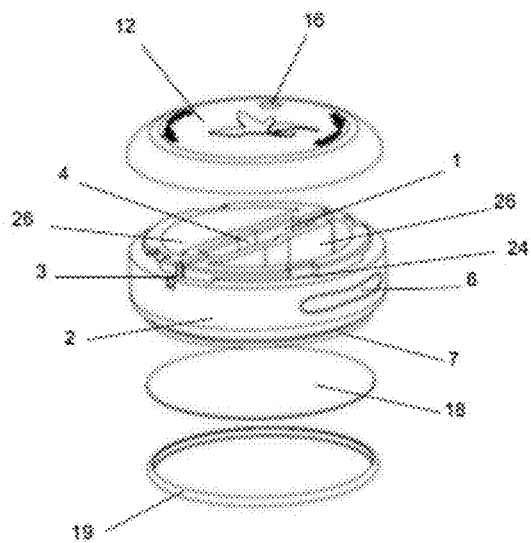
FIG. 12 shows a perspective bird's eye top view showing the overall assembly layout of a third illustrative embodiment that has a shelled out adapter base to reduce mass while maximizing ambient noise reduction.

FIG. 12 is a perspective bird's eye top view of the individual components of the unassembled stethoscope microphone adapter of an alternative embodiment. The embodiment in FIG. 12 also has twist-on lid similar to that of FIGS. 7-11. However, the twist-on lock-in grooves 24 for the lid protrusions 23 (FIG. 11) are recessed so that the edges of the lid 12 are flush with the circular sides of the base 2. The lid 12 of this embodiment contains a recessed small magnet 16 onto which an extraneous earbud can attach. Alternatively, the extraneous earbud can be placed into the groove 6 in the side of the base 2. The solid material on both sides of the microphone groove 1 and sound tunnel 4 has been shelled out in a semi-lunar fashion to form two mirroring cavities 26, thereby reducing the overall mass of the adapter. Note this embodiment also contains the widened diaphragm (60 mm in diameter).

Figure 13:
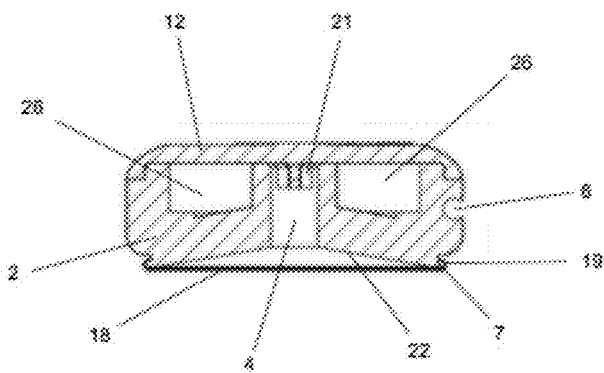
FIG. 13 shows a cross-sectional view of the third illustrative embodiment shown in FIG. 12 with the lid closed.

FIG. 13 is a coronal cross-sectional view through the center of the fully assembled embodiment in FIG. 12 with the twist-on lid 12 closed. When in locked position, the lid 12 forms a temporary seal around the grooves 1 and 3 (FIG. 12) for the microphone and attached wires, thereby forming a sealed sound chamber 21 that houses the microphone and facilitates optimal capture of desirable sound waves transmitted through the diaphragm 18. In this embodiment, much of the solid material comprising the base 2 has been removed to create two mirroring hollow cavities 26. The latter modification allows for reduction of the mass of the stethoscope adapter while maximizing the ambient noise reduction capabilities of the base 2.

Figure 14:
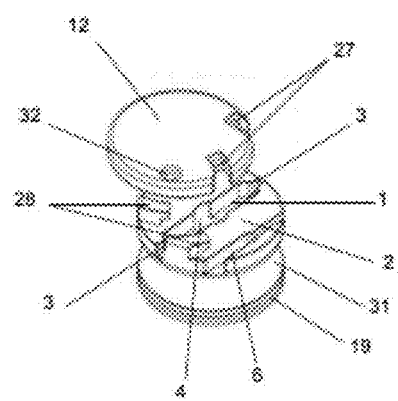
FIG. 14 shows a top view of a fourth illustrative embodiment of a fully assembled stethoscope microphone adapter with the lid in open position that includes a lid secured to the base by an ultra low profile screw from which the lid pivots and slides into its closed position.

FIG. 14 is a perspective bird's eye top view of a partially assembled stethoscope microphone adapter constructed in accordance with an alternative embodiment. The embodiment in FIG. 14 consists of a lid secured to the base by an ultra low profile screw 34 (FIGS. 18-20) from which the lid 12 pivots and slides into its closed position. The locking hooks 28 on the base 2 of the adapter assist with securing the lid 12 to the base 2 by sliding and fitting into the corresponding notches 27 on the lid 12. Note that the groove 6 for the extraneous earbud is located on the top surface of the base 2 of the adapter in this embodiment. Furthermore, the base 2 has sides 31 that are recessed to facilitate manual handling of the adapter.

Figure 15:
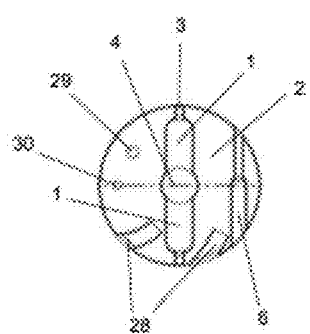
FIG. 15 shows a perspective top view of the base of the fourth illustrative stethoscope microphone adapter embodiment of FIG. 14.
Figure 19:
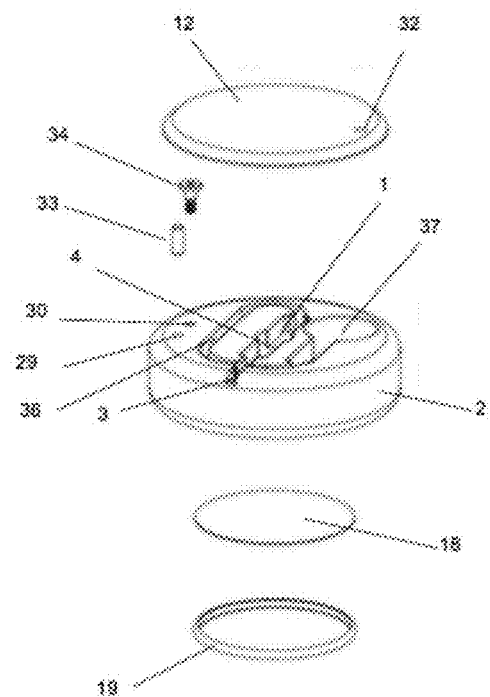
FIG. 19 shows a perspective top view showing the overall assembly layout of the fifth illustrative embodiment shown in FIG. 18.
Figure 20:
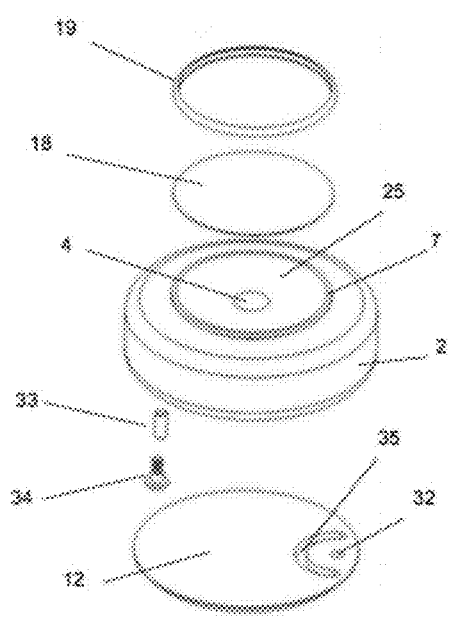
FIG. 20 shows a perspective bottom view showing the overall assembly layout of the fifth illustrative embodiment in FIG. 18 and FIG. 19, which include the smaller diaphragm (44 mm in diameter).

FIG. 15 is a perspective top view of the alternative embodiment in FIG. 14 with the sliding lid 12 (FIG. 14) removed to show the base 2 with its groove 1 for the microphone, grooves 3 for the wires attached to the microphone, and sound tunnel 4. The top surface of the base 2 contains a hole 29 for a dowel pin 33 (FIG. 19) that fits into a defined groove on the bottom of the lid 12 to limit its range of rotation. The top surface of the base 2 also contains a threaded hole 30 for the ultra low profile screw 34 (FIG. 18-20).

Figure 16:
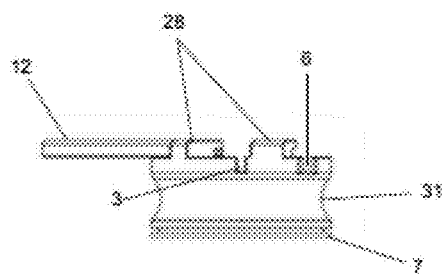
FIG. 16 shows a perspective side view of the lid and base of the fourth illustrative stethoscope microphone adapter embodiment shown in FIG. 13 through FIG. 15.

FIG. 16 is a perspective lateral view of the alternative embodiment in FIGS. 14 and 15 with the lid 12 in open position. Note the groove 6 for the extraneous earbud located on the top surface of the base 6 as well as the recessed sides 31 of the base 6. The locking hooks 28 become flush with the lid 12 when closed.

Figure 17:
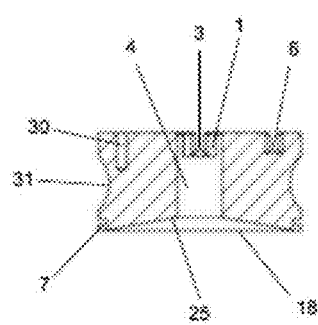
FIG. 17 shows a cross-sectional view of the fourth illustrative stethoscope microphone adapter embodiment without the without the lid shown in FIG. 13 through FIG. 16.

FIG. 17 is a sagittal cross-sectional view of the alternative embodiment in FIG. 14 without the lid 12 (FIGS. 14 and 16). As with the other embodiments, the widened sound tunnel 4 (9-11 mm in diameter) connects the groove 1 for the microphone with the small conical bottom 25 of the base 2. Note that this embodiment contains the small diaphragm 18 (44 mm in diameter).

Figure 18:
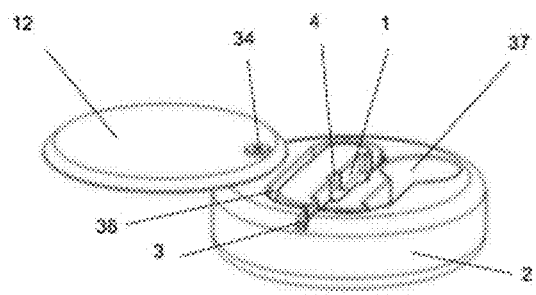
FIG. 18 shows a perspective top view showing the overall assembly layout of a fifth illustrative embodiment of the stethoscope microphone adapters, which includes a cap that pivots and slides into its closed position.

FIG. 18 is a perspective bird's eye top view of the fully assembled stethoscope microphone adapter constructed in accordance with an alternative embodiment. Similar to the embodiment in FIGS. 14-17, the embodiment in FIG. 17 has a sliding lid 12 that is secured to the base 2 by an ultra low profile shoulder screw 34, from which the lid 12 pivots into its open and closed positions in a horizontal plane. However, the base 2 of the embodiment in FIG. 18 has a predefined groove 36 to contain the length of the wire that connects the extraneous earbud to the microphone. The extraneous earbud then fits into the predefined cavity 37 within the base 2 and is completely contained and covered when the lid 12 is closed. Of note, this embodiment is vulnerable to an infinite feedback loop between the contained earbud and the microphone. However, this problem can be overcome by deactivation of the extraneous earbud with capable software.

FIG. 19 is a perspective bird's eye top view of the individual components of the unassembled stethoscope microphone adapter of the alternative embodiment in FIG. 18. The overall assembly is similar to that of the alternative embodiment shown in FIGS. 14-17. The lid 12 is secured to the base 2 by the ultra low profile shoulder screw 34, which fits through the hole 32 in the lid 12 and screws into the threaded hole 30 in the base 2. The dowel pin 33 fits into a hole 29 in the base and a predefined groove 35 (FIG. 20) on the bottom of the lid 12. The dowel pin 33 and the predefined groove 35 (FIG. 20) in the lid, therefore, restricts and defines the range of rotation of the lid 12.

FIG. 20 is a perspective bird's eye bottom view of the individual components of the unassembled stethoscope microphone adapter of the alternative embodiment in FIGS. 18 and 19. Note that the embodiments in FIGS. 18-20 contain the smaller diaphragm 18 (44 mm in diameter) and small conical bottom 25 of stethoscope adapter base.

Figure 21:
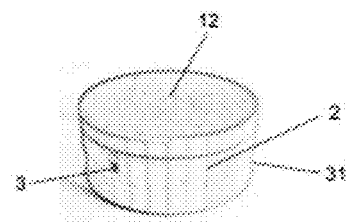
FIG. 21 is a perspective top view of a sixth illustrative embodiment of the stethoscope microphone adapters shown above.

FIG. 21 is a perspective bird's eye top view of the fully assembled stethoscope microphone adapter constructed in accordance with an alternative embodiment. In this embodiment, the lid has a protrusion 13 (FIG. 23) that fits and snaps into the groove 1 (FIG. 22) for the microphone and the groove 3 (FIG. 22) for wires that connect to the microphone of the pre-existing headset. This embodiment also has a recessed surface 31 on the side of the base 2 for fingers to facilitate manual handling of the adapter.

Figure 22:
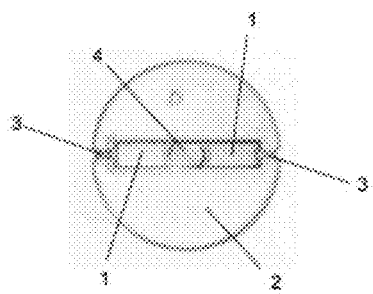
FIG. 22 is a top view of the base of the sixth illustrative embodiment of the stethoscope microphone adapter shown in FIG. 21.

FIG. 22 is a perspective top view of the base 2 of the stethoscope adapter with the lid removed revealing again the groove 1 for the microphone, grooves 3 for the wires connected to the microphone, and the sound tunnel 4 (9-11 mm in diameter).

Figure 23:
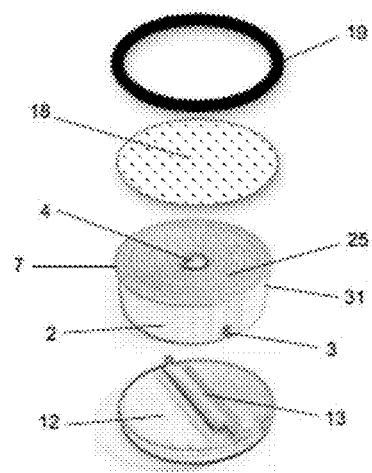
FIG. 23 is a perspective top view showing the overall assembly layout of the sixth illustrative embodiment of the stethoscope microphone adapters of FIG. 21 and FIG. 22.

FIG. 23 is a perspective bird's eye bottom view of the individual components of the unassembled stethoscope microphone adapter of the alternative embodiment in FIGS. 21 and 22. Note that the embodiments in FIGS. 21-23 contain a smaller diaphragm 18 (47 mm in diameter) and small conical bottom 25 of stethoscope adapter base.

In operation with the preferred embodiment (FIGS. 1-6), one places the microphone of the pre-existing earphone or headset listening device into the groove 1 of the base 2 of the stethoscope adapter. The wires extending from the ends of the microphone fit into a separate set of grooves 3 flanking the groove 1 for the microphone. The lid 12 is then closed about the hinge 14 so that the protrusion 13, which corresponds to the contour of the grooves for the microphone 1 and wires 3, covers the housed microphone to form a sealed sound chamber 21. The lid 12 is kept closed by the attraction of the recessed magnets in the lid 16 and in base 8. In alternative embodiments, such as that in FIGS. 7-13, the lid 12 does not have a hinge 14 that rotates around a clevis pin 20 secured to the base 2. Therefore, the protrusions 23 of the lid 12 in these alternative embodiments fit and slide into the complementary grooves 24 in the base 2 of the adapter with a manual twisting motion, thereby forming the sealed sound chamber 21. Alternatively, the groove channel may be on the lid 12 and the protrusions may be on the base 2. The alternative embodiments shown in FIGS. 14-20 have a lid 12 secured to the base 2 by an ultra low profile shoulder screw 34, from which the lid 12 pivots and slides in a horizontal plane against the base 2 into its closed and open positions. Finally, the bottom of the lid 12 of the alternative embodiment shown in FIGS. 21-23 has a protrusion 13, which snaps into the grooves 1 and 3 for the microphone and attached wires located on the base 2, as the lid closes to form the sealed sound chamber.

In the preferred (FIGS. 1-6) and some of the alternative (FIGS. 7-17) embodiments, an extraneous earbud 5 can be placed into a predefined groove 6 within the base 2 or lid 12 of the stethoscope adapter. In the other embodiment shown in FIGS. 18-20, the extraneous earbud and wire fits entirely into the predefined cavity 37 and groove 36 within the base 2 of the adapter. Alternatively, the extraneous earbud can attach to a recessed magnet 16 on the lid 12 (FIGS. 1-4, 12-13) on some of the embodiments. Following the placement of the stethoscope adapter onto the microphone, the earphone or headset listening device is then plugged into a 3.5 mm port of a device utilizing a CPU microprocessor. An app or software is launched to facilitate the capture, processing, and transmission of the sound data. Several apps that are capable of these functions are currently available at the time of this writing. Placement of the diaphragm 18 onto the surface of the body then enables capture of sounds by the housed microphone. Once the lid is closed, five effects transiently optimize capture of body sounds by the pre-existing microphone of a headset:

(1) In the embodiments with a widened diaphragm, the larger size of the diaphragm produces larger changes in air pressures resulting in louder sound waves that are captured.

(2) The material and thickness of the diaphragm influences the optimal frequencies of sound waves that are transmitted. The PETE plastic diaphragm less than 0.45 mm in thickness in the preferred embodiment permits transmission of low frequency sound waves, which is optimal for capturing biological sounds such as those of the heart, lungs, and bowel.

(3) The conical shape of the sound funnel and size of tunneling bore, through which the sound waves travel, filters undesirable ambient noise and amplifies the frequencies of sounds produced by body organs.

(4) The temporarily sealed sound chamber, which houses the microphone, prevents escape of sound waves, and therefore, maximizes the detection of the captured sound by the microphone.

(5) The material of the stethoscope adapter acts an insulator to further minimize detection of ambient sounds and loss of desirable sounds that are captured.

The sound signal, which is initially filtered by the diaphragm, conical base, and sound funnel, is finally detected by the housed microphone. The electrical signal produced by the microphone from the detected sounds can then be processed by the CPU in real-time for simultaneous listening with the available earbud, or the electrical signal can be processed by the CPU at a later time after the raw sound data is saved. Once the sounds of interest have been recorded, the saved file can then be transmitted via an internet cloud-based system or email in encrypted or unencrypted form. The primary intended use for the microphone stethoscope adapter is to facilitate telemedicine consultations by providing a cost-effective means of capturing and sending potentially diagnostic biological sounds from a patient to a healthcare provider in a remote location via the internet. The biological sounds that are targets for capture include heart, lung, bowel, and blood vessels of an individual as well as fetal heart sounds of a pregnant mother. The embodiment can be used by oneself on his/her own body, or it can be used by one individual to capture and listen to body sounds of another individual. Since the adapter utilizes the electrical components of a pre-existing headset with a smartphone or other type of computer that may already be readily available, the cost to manufacture will be significantly less than the currently available stand-alone electronic stethoscopes with integrated transducers. Furthermore, since the stethoscope adapter itself does not have electrical components, it is highly durable and resistant to water damage. Although the primary purpose of the stethoscope adapter is to increase the diagnostic capabilities of telemedicine, the ability to digitally record biological sounds and replay the recorded sounds to an audience also makes it a useful tool for teaching in the medical field as well as record keeping of biologic sounds for individuals as a private diary or to be shared later with a healthcare consultant.

After the sounds of interest have been captured, recorded, saved, and/or transmitted via the internet, the lid is opened easily for rapid removal of the stethoscope adapter so that the user can immediately return to its original use for the pre-existing headset, i.e., or music listening or conversational dialogue.

It is to be understood that the foregoing is a detailed description of illustrative embodiments. The scope of the claims is not limited to these specific embodiments. Various elements, details, execution of any methods, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A stethoscope system comprising:
   a. a grooved channel disposed in a base, the grooved channel configured to receive an inline microphone;
   b. a lid removably coupled to the base;
   c. a front diaphragm configured to contact a listening surface, wherein the front diaphragm is coupled to the base;
   d. a recessed surface disposed adjacent to the front diaphragm;
   e. a sound tunnel that includes a sound tunnel entrance proximate to the recessed surface, wherein the sound tunnel extends to the grooved channel;
   f. wherein the recessed surface and the sound tunnel are configured to capture sound vibrations received at the front diaphragm and transmit the sound vibrations through the sound tunnel to the inline microphone when the inline microphone is disposed in the grooved channel.

2. The system of claim 1, wherein:
   a. the inline microphone is permanently attached to the system;
   b. the inline microphone is wired as part of a head phone cable, the head phone cord having a first and a second earphone cord;
   c. the inline microphone is disposed on the first headphone cord thereby leaving the second headphone cord available for listening and transmission to a remote location.

3. The system of claim 1, wherein:
   a. the inline microphone is wired as part of a head phone cable, the head phone cable having a first end comprising a single cord and a second end comprising 2 cords each attached to an earphone;
   b. the microphone is disposed on the single cord.

4. The system of claim 1, wherein:
   a. the lid includes a hinge,
   b. the base includes one or more slots configured to receive the hinge.

5. The system of claim 1, further comprising:
   a. a retaining ring place inside a grooved clevis pin;
   b. a slotted opening in the base;
   c. a hole in the hinge;
   d. wherein the grooved clevis and retaining ring pin travel through the holes in the hinge and the slotted opening thereby securing base to the lid.

6. The system of claim 1, wherein the base includes a first magnet recessed into the base, and a second magnet recessed into the lid thereby allowing the lid to be removably coupled to the base via magnetic attraction between the first and second magnet.

7. The system of claim 1, the lid includes at least one magnet disposed on an outer surface of the lid thereby allowing earbuds to magnetically attach to and remove from the lid.

8. The system of claim 1, wherein the lid includes a protrusion shaped to correspond to the grooved channel such that when the lid is closed a sealed sound chamber is formed about the inline microphone.

9. The system of claim 1, wherein the diaphragm is secured to a bottom notched edge of the base by a concave semi-flexible ring made from a material selected from the group consisting of rubber, silicone, and plastic.

10. The system of claim 1, wherein the diaphragm is secured to the base via adhesive tape.

11. The system of claim 1, wherein a bottom side of the base is of a wide conical shape, thereby facilitating optimal capture of the sound vibrations.

12. The system of claim 1, wherein the diaphragm is composed of polyethylene terephthalate.

13. The system of claim 12, wherein the thickness of the diaphragm is less than 0.45 millimeters.

14. The system of claim 1, wherein the lid is configured to twist on to and off of the base.

15. The system of claim 1, wherein the base contains a groove configured to fit extraneous earbuds.

16. The system of claim 1, wherein the lid contains a groove configured to fit extraneous earbuds.

17. The system of claim 1, further comprising a computing device connected to the inline microphone, the computing device is configured to convert the sound vibrations into digital data.

18. The system of claim 17, wherein the computing device is further configured to provide heart rate data when the listening surface is proximate to a beating heart.

19. The system of claim 17, wherein the computing device is further configured to provide heart rhythm data when the listening surface is proximate to a beating heart.

20. The system of claim 17, wherein the computing device is further configured to provide heart murmur data when the listening surface is proximate to a beating heart.

21. The system of claim 17, wherein the computing device is configured to provide graphic visualization of the sound vibrations.

22. The system of claim 17, wherein the computing device is capable of transmitting the digital data to a remote location via internet.

23. The system of claim 17, wherein the computing device is configured to store the data.

24. The system of claim 17, wherein the computing device is selected from the group consisting of a computer, a smartphone, and a tablet.

25. The system of claim 1, wherein the listening surface comprises a part of a human body.

26. A stethoscope system comprising:
   a. a grooved channel disposed in a lid, the grooved channel configured to receive an inline microphone;
   b. the lid removably coupled to a base;
   c. a front diaphragm configured to contact a listening surface, wherein the front diaphragm is coupled to the base;
   d. a recessed surface disposed adjacent to the front diaphragm;
   e. a sound tunnel that includes a sound tunnel entrance proximate to the recessed surface, wherein the sound tunnel extends to the grooved channel when the lid is closed;
   f. wherein the recessed surface and the sound tunnel are configured to capture sound vibrations received at the front diaphragm and transmit the sound vibrations through the sound tunnel to the inline microphone when the inline microphone is disposed in the grooved channel.

27. The system of claim 26, wherein the base includes a protrusion shaped to correspond to the grooved channel such that when the lid is closed a sealed sound chamber is formed about the inline microphone.

* * * * *